United States Patent [19]

Hashimoto et al.

[11] Patent Number: 4,464,539

[45] Date of Patent: Aug. 7, 1984

[54] PROCESS FOR PRODUCING α,β-UNSATURATED CARBOXYLIC ACIDS OR ESTERS THEREOF

[75] Inventors: Masao Hashimoto, Yokohama; Tadatoshi Honda, Fujisawa, both of Japan

[73] Assignee: Mitsui Toatsu Chemicals, Inc., Tokyo, Japan

[21] Appl. No.: 480,779

[22] Filed: Apr. 6, 1983

Related U.S. Application Data

[63] Continuation of Ser. No. 311,600, Oct. 15, 1981, abandoned.

[30] Foreign Application Priority Data

Oct. 16, 1980 [JP] Japan .................. 55-143591

[51] Int. Cl.$^3$ .............. C07C 67/327; C07C 67/20; C07C 51/06; C07C 51/377
[52] U.S. Cl. .................. 560/212; 562/599; 260/410.9 R; 260/413; 502/208
[58] Field of Search .............. 560/205, 214, 212, 215; 562/599; 502/208; 260/410.9 Q, 413 Q, 413 R

[56] References Cited

U.S. PATENT DOCUMENTS

| | | | |
|---|---|---|---|
| 1,820,208 | 10/1931 | Bauer | 560/212 |
| 2,183,357 | 12/1939 | Ritchie et al. | 560/212 |
| 2,859,240 | 11/1958 | Holmen | 560/212 |
| 3,022,336 | 2/1962 | Sennewald et al. | 560/212 |
| 3,022,337 | 2/1962 | Enk et al. | 560/212 |
| 3,022,338 | 2/1962 | Enk et al. | 560/212 |
| 3,644,497 | 2/1972 | Mesich | 560/205 |
| 4,018,816 | 4/1977 | Onoda et al. | 560/205 |
| 4,161,609 | 7/1979 | Cramer | 560/215 |

OTHER PUBLICATIONS

Kirk–Othmer, *Encyclopedia of Chemical Technology*, 2nd Ed. Interscience, Publ., vol. 2, (1964), at p. 69 and vol. 8, (1965), at p. 339.

Degering, Ed. F., *An Outline of Organic Nitrogen Compounds*, (1950), Univ. Lithoprinters, Ypsilanti, Mich., pp. 409–410.

Nakayama, Yukio et al., *Chemical Abstracts*, vol. 72, (1970), #100,060g, (Abstract of Japan, 70-04,971).

*Primary Examiner*—Natalie Trousof
*Assistant Examiner*—L. Hendriksen
*Attorney, Agent, or Firm*—Fisher, Christen & Sabol

[57] ABSTRACT

A process for producing an α,β-unsaturated carboxylic acid or esters thereof which comprises bringing an α-hydroxycarboxylic acid amide into contact with a solid acid catalyst independently or along with water, or along with water and an aliphatic alcohol, or along with an aliphatic alcohol.

16 Claims, 1 Drawing Figure

PROCESS FOR PRODUCING α,β-UNSATURATED CARBOXYLIC ACIDS OR ESTERS THEREOF

This application is a continuation, of application Ser. No. 311,600, filed Oct. 15, 1981, now abandoned.

BACKGROUND OF THE INVENTION

This invention relates to a process for producing an α,β-unsaturated carboxylic acid or esters thereof by contacting an α-hydroxycarboxylic acid amide independently with a solid acid catalyst, or along with water and/or an aliphatic alcohol.

A process for producing the α,β-unsaturated carboxylic acid esters, for example, methyl methacrylate on a commercial scale, comprises reacting acetone cyanohydrin with concentrated sulfuric acid to form methacrylamide sulfate and thereafter esterifying this with methanol.

This process however has numerous drawbacks including, for example, the corrosion of the apparatus by the concentrated sulfuric acid, the necessity for treating the ammonium sulfate of low value that is produced in large quantities as a by-product, and the need to cope with the pollution that results from the spent sulfuric acid.

BROAD DESCRIPTION OF THE INVENTION

It is therefore an object of this invention to produce the α,β-unsaturated carboxylic acids or the esters thereof using cyanohydrin as the starting material and without using sulfuric acid.

The foregoing object can be achieved by a process which comprises using an α-hydroxycarboxylic acid amide obtained by the hydration reaction of cyanohydrin and contacting this amide alone with a solid acid catalyst, or along with water and/or an aliphatic alcohol.

The process for producing the α,β-unsaturated carboxylic acids or the esters thereof by the dehydration reaction of the α-hydroxycarboxylic acid esters is known (Japanese Patent Publication No. 4971/70). However, a process which uses an α-hydroxycarboxylic acid amide, as in this invention, is not yet known.

The following advantages are had by the new process of this invention. (1) A new use as an industrial raw material has been found for the α-hydroxycarboxylic acid amides that can be readily produced in high yield by the hydration of cyanohydrin in the presence of a manganese dioxide catalyst (U.S. Pat. No. 3,366,639). (2) The reaction for synthesizing the α,β-unsaturated carboxylic acids or their esters from the α-hydroxycarboxylic acid amides is a complicated reaction system. It sets up such reactions as the formation of unsaturated bonds by a dehydration reaction, the formation of the carboxyl group by the hydrolysis of the amido group, and the formation of carboxylic esters by an esterification reaction, while at the same time ammonia and alkylamines are formed. The process of this invention can however produce the α,β-unsaturated carboxylic acids and the esters thereof in good yields with no such troubles as objectionable decomposition and polymerization reactions. Further, (3) the nitrogen component contained in the starting material is not taken out as a by-product of low value, such as ammonium sulfate, but as alkylamines and ammonia that are commercially valuable as intermediates.

One of the preferred modes of practicing the invention comprises contacting an α-hydroxycarboxylic acid amide and water with a first solid acid catalyst, and thereafter carrying out a reaction by contacting the resulting reaction mixture with a second solid acid catalyst along with an aliphatic alcohol to form an α, β-unsaturated carboxylic acid ester, it is also possible to almost completely inhibit the formation as a by-product of ethers that result from the dehydration reaction of the aliphatic alcohol.

SUMMARY OF THE INVENTION

The production of α,β-unsaturated carboxylic acids or esters thereof in high yield without using corrosive sulfuric acid is achieved by contacting an α-hydroxycarboxylic acid amide with a solid acid catalyst. When the intended product is an α,β-unsaturated carboxylic acid, the amide reactant is catalytically reacted alone or with water. When the intended product is an α,β-unsaturated carboxylic acid ester, the amide reactant is catalytically reacted with an aliphatic alcohol. Conjoint use of water and the aliphatic alcohol produces both the α,β-unsaturated carboxylic acid and ester. The α,β-unsaturated carboxylic acid esters are preferably produced by catalytically reacting the amide with a first solid acid catalyst, preferably in the presence of water, followed by catalytically reacting the resulting reaction mixture with a second solid acid catalyst along with an aliphatic alcohol. The amide reactants used in the present invention are of the formula

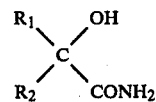

wherein $R_1$ and $R_2$ are each hydrogen or an alkyl group, with the proviso that at least one of $R_1$ and $R_2$ is an alkyl group.

BRIEF DESCRIPTION OF THE DRAWING

The sole FIGURE shows an apparatus for conducting a two-stage catalytic reaction in accordance with the process of the present invention.

DETAILED DESCRIPTION OF THE INVENTION

Figure 1:
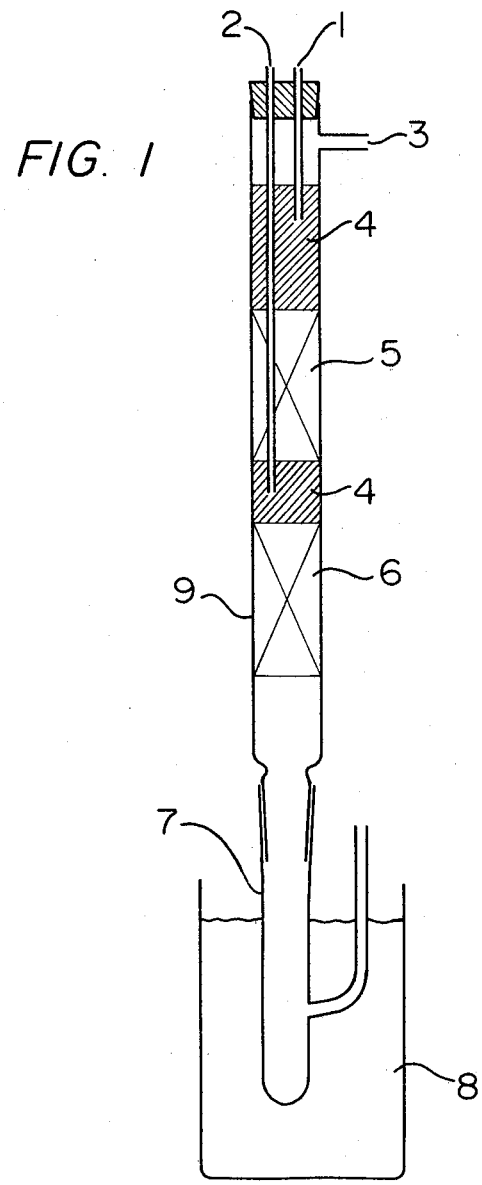

The α-hydroxycarboxylic acid amides used are compounds of the general formula

wherein $R_1$ and $R_2$ are each hydrogen or an alkyl group, with the proviso that at least one is an alkyl group.

Specific examples of these compounds are say lactamide, α-hydroxybutyramide, α-hydroxyisobutyramide, α-hydroxyvaleramide, α-hydroxyisovaleramide, α-methyl-α-hydroxybutyramide and α,γ-dimethyl-α-hydroxybutyramide, of which most frequently used are lactamide and α-hydroxyisobutyramide.

Next, the aliphatic alcohols are, for example, the aliphatic alcohols of 1–4 carbon atoms such as methyl alcohol, ethyl alcohol, n-propyl alcohol, i-propyl alcohol, n-butyl alcohol, i-butyl alcohol, t-butyl alcohol, ethylene glycol, ethylene glycol monomethyl ether, propylene glycol and propylene glycol monomethyl ether, of which preferred are methyl alcohol, ethyl alcohol, n-propyl alcohol, i-propyl alcohol, n-butyl alcohol, i-butyl alcohol and t-butyl alcohol.

When it is intended to obtain an $\alpha,\beta$-unsaturated carboxylic acid by the process of this invention, the aforesaid $\alpha$-hydroxycarboxylic acid amide or the $\alpha$-hydroxycarboxylic acid amide and water are catalytically reacted with a solid acid catalyst. On the other hand, when it is intended to obtain an $\alpha,\beta$-unsaturated carboxylic acid ester, the $\alpha$-hydroxycarboxylic acid amide is catalytically reacted with a solid acid catalyst along with an aliphatic alcohol or both an aliphatic alcohol and water. Alternatively, the $\alpha$-hydroxycarboxylic acid amide or the $\alpha$-hydroxycarboxylic acid amide and water are catalytically reacted with a first solid acid catalyst, after which the resulting reaction mixture is catalytically reacted with a second solid acid catalyst along with an aliphatic alcohol.

Usable as the solid acid catalyst are at least one compound selected from the phosphates, sulfates and oxides of metallic elements and nonmetallic elements of groups IIIa, IVa and Va of the periodic table of elements, and catalysts containing at least one of the foregoing compounds, active carbon, cation-exchange resins, $\alpha$-boron and metallic nickel, as well as the solid phosphoric acid catalyst. The solid phosphoric acid catalyst is specifically a catalyst obtained by depositing phosphoric acid on a known carrier, for example, diatomaceous earth followed by subjecting the supported catalyst to a suitable calcination treatment.

The phosphate, the catalyst component of the solid acid catalyst used, is at least one phosphate of an element (m) selected from the group consisting of the groups Ia, Ib, IIa, IIb, IIIa, IIIb, lanthanide, actinide, IVa, IVb, Va, Vb, VIb, VIIb, and VIII of the long form of the periodic table, e.g., Li, Na, K, Rb, Cs, Be, Mg, Ca, Sr, Ba, Sc, Y, La, Ce, Pr, Nd, Sm, Gd, Th, U, Ti, Zr, Hf, V, Nb, Ta, Cr, Mo, W, Mn, Fe, Co, Ni, Cu, Ag, Zn, Cd, B, Al, Ga, In, Tl, Sn, Pb, Sb and Bi.

The foregoing element (M) and phosphorus (P) are contained in the phosphate in an atomic ratio (M/P) not exceeding 3. As long as this range is satisfied, there is imposed no restriction as to the structure of the phosphate.

The phosphate can be prepared by any known method.

On the other hand, the sulfate, another catalyst component, is a sulfate or acid sulfate of an element selected from the groups Ia, Ib, IIa, IIb, IIIa, IVa, VIb, VIIb and VIII, for example, Li, Na, K, Rb, Cs, Be, Mg, Ca, Sr, Ba, Cr, Mn, Fe, Co, Ni, Cu, Zr, Cd, Al, In, Sn and Rb.

The metal oxide, still another catalyst component, is an oxide of a metallic element selected from Be, Mg, Y, La, Ce, Th, U, Ti, Zr, V, Cr, Mo, W, Mn, Fe, Co, Ni, Cu, Zn, Cd, B, Al, Si, Sb and Bi, and it may be a compound oxide in which two or more of these metallic elements are present.

The foregoing phosphates, sulfates or metal oxides can be used as catalyst by using these compounds as such either singly or in admixture of two or more. Besides these, there is also a catalyst obtained by mixing one or more phosphates as major components with sulfates and metal oxides as minor components, after which the resulting mixture is mixed with such commonly known carriers as active carbon, silica, silica-alumina and alumina by such known procedures as mixing and kneading or dipping. On the other hand, a catalyst containing sulfates, is obtained by such procedures as mixing one or more sulfates, or a mixture containing one or more sulfates as major components and metal oxides and phosphates as minor components, with known carriers such as mentioned hereinabove, and treating the mixture by the known mixing and kneading or dipping procedures. Further, a catalyst containing the metal oxides, is obtained by mixing or more metal oxides, or a mixture containing one or more metal oxides as major components and phosphates or sulfates as minor components, with a carrier such as mentioned hereinabove, and thereafter treating the mixture by the precipitation or dipping method.

As indicated hereinbefore, the $\alpha,\beta$-unsaturated carboxylic acids can be obtained in accordance with the process of this invention by catalytically reacting an $\alpha$-hydroxycarboxylic acid amide independently, or along with water, with a solid acid catalyst; or the $\alpha,\beta$-unsaturated carboxylic acid esters can be obtained by catalytically reacting an $\alpha$-hydroxycarboxylic acid amide with a solid acid catalyst along with an aliphatic alcohol, or with both water and an aliphatic alcohol. However, in a preferred mode of practicing the invention process, the $\alpha,\beta$-unsaturated carboxylic acid esters can be obtained by a process which comprises catalytically reacting an $\alpha$-hydroxycarboxylic acid amide with a first solid acid catalyst preferably in the presence of water, followed by catalytically reacting the resulting reaction mixture with a second solid acid catalyst along with an aliphatic alcohol.

The first and second solid acid catalysts used in the foregoing mode may be the same or different, so long as they are catalysts selected from the hereinbeforementioned solid acid catalysts. They may be used in such a manner that the contact with the reactants takes place separately and at a different time during the time the reaction proceeds.

Preferred as the first solid acid catalyst are however those catalysts containing at least one compound chosen from the class consisting of a phosphate of an element of groups Ia, IIa, IIIa, IIIb, lanthanide, actinide, Va and VIIb, a compound oxide of silicon oxide and an oxide of an element of group IIa or IIb, and a compound oxide of an oxide of an element of group IVb and an oxide of an element of group IIb or IVa. For example, included are those catalysts containing aluminum phosphate, magnesium phosphate, sodium phosphate, yttrium phosphate, lanthanum phosphate, cerium phosphate, praseodymium phosphate, barium phosphate, bismuth phosphate, calcium phosphate, manganese phosphate, sodium magnesium phosphate, a compound oxide of zinc oxide and silicon oxide, a compound oxide of magnesium oxide and silicon oxide, a compound oxide of titanium oxide and magnesium oxide, and a compound oxide of zirconium oxide and tin oxide. Especially preferred of these compounds are yttrium phosphate, lanthanum phosphate, cerium phosphate, praseodymium phosphate, aluminum phosphate, magnesium phosphate, and a compound oxide of magnesium oxide and silicon oxide.

On the other hand, preferred as the second solid acid catalyst are those catalysts containing at least one compound chosen from the class consisting of a phosphate of an element of groups IIIa, IVb, VIb and iron, an oxide of an element of group IVb, and a compound oxide of silicon oxide and an oxide of an element of group IIIa or IVb. Examples include the catalysts containing aluminum phosphate, iron phosphates, molybdenum phosphate, tungsten phosphate, titanium phosphate, zirconium phosphate, titanium oxides, zirconium oxide, a compound oxide of aluminum oxide and silicon oxide, a compound oxide of titanium oxides and silicon oxide, and a compound oxide of zirconium oxide and silicon oxide. Especially preferred of these catalysts are those containing zirconium phosphate, titanium phosphate, titanium oxides or zirconium oxide.

When an $\alpha,\beta$-unsaturated carboxylic acid or an $\alpha,\beta$-unsaturated carboxylic acid ester is to be produced from an $\alpha$-hydroxycarboxylic acid amide by the one-stage process of this invention, the reaction is carried out in the following manner.

The class of the starting reactants and the amounts in which they are used varies depending upon whether the intended product is obtained as an $\alpha,\beta$-unsaturated carboxylic acid, its ester or a mixture thereof.

When the intended product is an $\alpha,\beta$-unsaturated carboxylic acid, an $\alpha$-hydroxycarboxylic acid amide, preferably an $\alpha$-hydroxycarboxylic acid amide and water are used as the starting materials, and there is no need to use an aliphatic alcohol. The amount of water is usually 0-200 moles, and preferably 1-50 moles, per mole of the $\alpha$-hydroxycarboxylic acid amide. On the other hand, when the intended product is an $\alpha,\beta$-unsaturated carboxylic acid ester, an $\alpha$-hydroxycarboxylic acid amide and an aliphatic alcohol are used as the starting materials. The amount of the aliphatic alcohol used is not more than 200 moles, and preferably 1-50 moles, per mole of the $\alpha$-hydroxycarboxylic acid amide. Conjoint use of water with the aliphatic alcohol is also permissible. In this case, an $\alpha,\beta$-unsaturated carboxylic acid is also formed in addition to the $\alpha,\beta$-unsaturated carboxylic acid ester. The proportion of the products (ester and acid) will vary depending upon the proportion of the starting materials used, the catalyst used, the reaction temperature and time. Hence, the reaction conditions are chosen in accordance with what products are intended.

The reaction temperature is 150°-500° C., and preferably 200°-450° C. While usually a reaction pressure of normal atmospheric pressure will do, the reaction may also be carried out at superatmospheric or reduced pressure.

The reaction may be carried out in either the vapor, liquid, or vapor-liquid mixed phase, so long as it is a method in which contact is achieved between the reactants and the solid acid catalyst. Usually preferred is either the vapor or vapor-liquid mixed phase, which is carried out by the fixed bed or fluidized bed process.

When the reaction is carried out in the vapor phase, the rate at which the reactants are fed can be varied over a wide range depending upon such reaction conditions as the catalyst used, the reaction temperature, etc., but usually a liquid hourly space velocity in the range of 0.005-10/hr should be sufficient. Further, in carrying out the reaction, the contact of the starting reaction materials with the catalyst layer can be carried out in an inert gas such as nitrogen or carbon dioxide. Again, as required, the reaction may be initiated after first having fed ammonia or ammonia water to the catalyst layer for pretreating the catalyst.

In a preferred process of this invention, the $\alpha,\beta$-unsaturated carboxylic acid esters can be produced by a two-stage process, as mentioned hereinbefore. To wit, it is a process comprising contacting an $\alpha$-hydroxycarboxylic acid amide, preferably an $\alpha$-hydroxycarboxylic acid amide and water, with a first solid acid catalyst, followed by contacting the resulting reaction mixture with a second solid acid catalyst along with an aliphatic alcohol to yield an $\alpha,\beta$-unsaturated carboxylic acid ester. In this process, as indicated hereinabove, the $\alpha$-hydroxycarboxylic acid amide, preferably the $\alpha$-hydroxycarboxylic acid amide and water, are first catalytically reacted with a first solid acid catalyst. The amount of water used ranges from 0 to 200 moles, preferably from 1 to 50 moles, per mole of the $\alpha$-hydroxycarboxylic acid amide. The reaction temperature is 150°-500° C., preferably 200°-450° C. While a reaction pressure of usually normal atmospheric pressure will do, the reaction may also be carried out under superatmospheric or reduced pressure. When the reaction is carried out in the vapor phase, the rate at which the reactant is fed can be varied over a wide range depending upon the catalyst used, the reaction temperature, etc., but usually a liquid hourly space velocity in the range of 0.005-10/hr should be sufficient.

There is no special need to separate the product from the resulting reaction mixture. After adding an aliphatic alcohol to the as-obtained reaction mixture, it is catalytically reacted with a second solid acid catalyst to give an $\alpha,\beta$-unsaturated carboxylic acid ester.

The aliphatic alcohol is added to the reaction mixture in an amount of not more than 200 moles, preferably 1-50 moles. The reaction temperature, reaction pressure and liquid hourly space velocity may be in the same ranges as in the first stage. If these are within these ranges, the individual reaction conditions may be the same or different.

Further, in carrying out the reaction in the vapor phase, an inert gas such as nitrogen or carbon dioxide may be entrained in the starting reaction material. Again, the catalysts may, as required, be pretreated by feeding ammonia or ammonia water to the catalyst layer.

The following examples will serve to illustrate the present invention more specifically.

The formula denoting the catalyst containing a phosphate used in the examples is not necessarily one that shows the structure of the phosphate contained in the catalyst, but is one that shows the atomic ratio of the aforementioned metal to phosphorus (M/P). For example, even though the phosphate under reaction conditions is one having a condensed phosphate structure of say metaphosphate and pyrophosphate, the formula denoting the catalyst has been shown as that of the corresponding orthophosphate.

EXAMPLE 1

An aqueous solution (100 cc) containing 15 g (0.13 mole) of 85% phosphoric acid was added with stirring to 400 cc of an aqueous solution containing 50 g (0.13 mole) of yttrium nitrate hexahydrate. The mixture was concentrated by heating to yield a paste, which was dried at 120° C. The paste was then calcined at 400° C. for 5 hours in a stream of air followed by molding it into granules of a 10-16-mesh size. Five cc of the YPO$_4$ catalyst thus prepared was packed in a Pyrex reaction tube of 12-mm inside diameter and fixed in an electric furnace held at 275° C. Next, while causing nitrogen to flow into the tube from its top at a gas space velocity of 120 liter/liter/hr, 14% ammonia water was passed through the catalyst layer at a liquid hourly space velocity of 0.5 liter/liter/hr for 30 minutes. The feed of ammonia water was then stopped, and a methanol solution containing 13.7% of α-hydroxyisobutyramide was fed at a liquid hourly space velocity of 0.26 liter/liter/hr. The gas leaving the catalyst layer was separated into a condensed product and a noncondensed product at a dry ice trap coupled to the bottom of the reaction tube, following which the products obtained were quantitatively analyzed by gas chromatography and chemical analysis. The molar yield of methyl methacrylate based on the starting α-hydroxyisobutyramide was 87.5%.

EXAMPLE 2

Lanthanum oxide ($La_2O_3$) (212 g, 0.065 mole) was completely dissolved in an aqueous nitric acid solution, after which the solution was concentrated by heating to prepare lanthanum nitrate, to which was added water to give 400 cc of an aqueous lanthanum nitrate solution.

Next, when 100 cc of an aqueous solution containing 20.3 g (0.143 mole) of sodium hydrogenphosphate ($Na_2HPO_4$) was added, a white precipitate was formed. After stirring this at 80° C. for one hour, the white precipitate was thoroughly water-washed by the decantation method followed by separation by filtration and water-washing. The resulting white precipitate was dried at 120° C., calcined at 400° C. for 6 hours in a stream of air, and thereafter molded into granules of 10–16-mesh size. The $LaPO_4$ catalyst (5 cc) thus obtained was packed in a Pyrex reaction tube of 12-mm inside diameter, which then was secured in an electric furnace held at 275° C. Next, while passing nitrogen from the top of the reaction tube through the catalyst layer at a gas space velocity of 480 liter/liter/hr, 14% ammonia water was passed through the catalyst layer at a liquid hourly space velocity of 0.5 liter/liter/hr for 30 minutes. The feed of the ammonia water was then stopped, and a feed liquid consisting of α-hydroxyisobutyramide, methanol and water in a mole ratio of 1:14:11.5 was fed at a liquid hourly space velocity of 0.26 liter/liter/hr. The gas leaving the catalyst layer was trapped in a dry ice trap coupled to the bottom of the reaction tube. When the products were quantitatively analyzed by gas chromatography, the molar yields of methyl methacrylate and methacrylic acid were 83.2% and 3.0%, respectively, based on the starting α-hydroxyisobutyramide.

EXAMPLE 3

The reaction apparatus used in Example 1 was used, and the reactions were carried out while varying the catalyst and reaction conditions. Of the catalysts used, $P_2O_5$ $24MoO_3$, $AlPO_4$, $FePO_4$, $Pb_3(PO_4)_2$ and $Al(H_2PO_4)$ were commercially available reagents that were used after molding or depositing on a carrier and calcination. The other catalysts were prepared by the usually known methods. To wit, a metal nitrate, metal chloride or metal oxide and 85% phosphoric acid or a phosphate were taken in amounts such that the atomic ratio of metal to phosphorus would be that indicated. After directly reacting these components in an aqueous solution, the reaction product was evaporated to dryness, or the solid obtained by separating the resulting phosphate from the aqueous solution and water-washing was thoroughly dried at 120° C. The phosphates thus prepared and the commercial phosphates were molded into pellets and calcined at 250°–600° C. for 5 hours. The catalyst was then obtained by crushing the calcined pellets into granules of 10–16-mesh size.

In carrying out the reaction, nitrogen was fed to the catalyst layer as a diluent or carrier gas at a gas space velocity of 120 liter/liter/hr.

Further, as a pretreatment of the catalyst, 14% ammonia water was fed at a liquid hourly space velocity of 0.5 liter/liter/hr for 30 minutes at the reaction temperature. The reaction was then carried out using the following feed liquids A–F.

Feed liquid composition (molar ratio)
A. α-hydroxyisobutyramide:methanol=1:20
B. ditto:ditto:water=1:14:11.5
C. ditto:water=1:20
D. lactamide:methanol=1:17
E. ditto:ditto:water=1:10:8
F. ditto:water=1:17

The gas leaving the catalyst layer was trapped at a dry ice trap, and the products were quantitatively analyzed by gas chromatography. In Table 1 are shown the catalyst used, reaction conditions, class of feed liquid, its rate of feed, and the product and its yield. The yield of the product is shown as molar yield (%) based on the starting α-hydroxycarboxylic acid amide.

TABLE 1

| Run | Catalyst | Feed liquid | LHSV (hr$^{-1}$) | Reaction temperature (°C.) | Product | Yield of product (%) |
|---|---|---|---|---|---|---|
| 1 | $NdPO_4$ | A | 0.26 | 375 | methyl methacrylate | 76.5 |
| 2 | $YCePO_4$ | A | 0.26 | 400 | " | 75.1 |
| 3 | $PrPO_4$ | B | 0.26 | 300 | " | 81.7 |
| 4 | $Ce_2(HPO_4)_3$ | B | 0.33 | 275 | " | 63.3 |
| 5 | $La_2(HPO_4)_3$ | B | 0.65 | 300 | " | 79.0 |
| 6 | $ZrPO_4(Zr/P = 1/1)$ | B | 0.26 | 275 | " | 45.2 |
| 7 | $Cd_3(PO_4)_2\cdot 2CdHPO_4$ | B | 0.65 | 350 | " | 30.3 |
| 8 | $LiBePO_4$ | B | 0.26 | 390 | " | 38.7 |
| 9 | $La_2(HPO_4)_3$ | C | 0.52 | 300 | methacrylic acid | 84.8 |
| 10 | $LaPO_4$ | C | 1.3 | 300 | " | 82.3 |
| 11 | $Mn(NH_4)PO_4$ | C | 0.26 | 300 | " | 73.5 |
| 12 | solid phosphoric acid/$SiO_2\cdot Al_2O_3$ | C | 0.26 | 325 | " | 40.8 |
| 13 | $BPO_4$ | C | 0.26 | 300 | " | 43.4 |
| 14 | $YSb(PO_4)_2$ | C | 0.26 | 325 | " | 74.1 |
| 15 | $SnHPO_4$ | C | 0.26 | 350 | " | 15.2 |
| 16 | $CoHPO_4$ | C | 0.26 | 350 | " | 34.6 |
| 17 | $YGd(PO_4)_2$ | D | 0.26 | 375 | methyl acrylate | 71.3 |
| 18 | $P_2O_5\cdot 24MoO_5/SiO_2$ | D | 0.52 | 375 | " | 38.7 |
| 19 | $Zr_3(PO_4)_4$ | D | 0.26 | 300 | " | 40.8 |

TABLE 1-continued

| Run | Catalyst | Feed liquid | LHSV (hr$^{-1}$) | Reaction temperature (°C.) | Product | Yield of product (%) |
|---|---|---|---|---|---|---|
| 20 | AlPO$_4$ | D | 0.26 | 375 | " | 73.0 |
| 21 | TiPO$_4$(Ti/P = 1/1) | E | 0.26 | 275 | " | 48.3 |
| 22 | NiHPO$_4$ | E | 0.26 | 350 | " | 29.7 |
| 23 | CuHPO$_4$ | E | 0.26 | 350 | " | 36.1 |
| 24 | GaPO$_4$ | E | 0.26 | 350 | " | 41.0 |
| 25 | CrPO$_4$ | F | 0.26 | 275 | acrylic acid | 61.9 |
| 26 | FePO$_4$ | F | 0.26 | 325 | " | 58.7 |
| 27 | BiPO$_4$ | F | 0.26 | 350 | " | 41.5 |
| 28 | ZnHPO$_4$ | F | 0.26 | 325 | " | 37.4 |
| 29 | Cu$_3$(PO$_4$)$_2$ | F | 0.26 | 350 | " | 40.5 |
| 30 | Pb$_3$(PO$_4$)$_2$ | F | 0.26 | 350 | " | 8.0 |
| 31 | Al(H$_2$PO$_4$)$_3$ | F | 0.26 | 325 | " | 28.8 |
| 32 | AlPO$_4$ | F | 0.26 | 375 | " | 80.2 |

EXAMPLE 4

A K$_3$PO$_4$ catalyst, a Ca$_3$(PO$_4$)$_2$ catalyst, a MgHPO$_4$ catalyst, a CaHPO$_4$ catalyst, a NaH$_2$po catalyst and a KH$_2$PO$_4$ catalyst were prepared by the following method. The several commercial reagents, i.e., the potassium tertiary phosphate, calcium tertiary phosphate, magnesium secondary phosphate, calcium secondary phosphate, sodium primary phosphate and potassium primary phosphate reagents were calcined at 500° C. for 6 hours and thereafter molded into granules of 10–16-mesh size to give the several catalysts. On the other hand, the catalysts consisting of these reagents supported on a carrier were prepared in the following manner. For example, 60 parts of silica to be used as carrier were comminuted to granules of 10–16-mesh size, to which was added 40 parts of the phosphate (calculated on a dry basis), following which the silica and phosphate were thoroughly mixed with the addition of water. The mixture was then evaporated to dryness and calcined at 500° C. for 6 hours to prepare the catalyst.

A LiH$_2$PO$_4$ catalyst, a RbH$_2$PO$_4$ catalyst, a CsH$_2$PO$_4$ catalyst, a Cs$_2$HPO$_4$ catalyst, a BeHPO$_4$ catalyst, a SrHPO$_4$ catalyst, a Mg$_{0.5}$H$_2$PO$_4$ catalyst, a Ba$_{0.5}$H$_2$PO$_4$ catalyst, a Na$_{0.5}$Mg$_{0.25}$H$_2$PO$_4$ catalyst and a NaMg$_{0.5}$HPO$_4$ catalyst were prepared in the following manner. Lithium tertiary phosphate, rubidium carbonate, cesium carbonate, beryllium oxide, magnesium oxide, strontium hydroxide, barium hydroxide, sodium hydroxide and 85% phosphoric acid were mixed in accordance with the several catalyst compositions along with water. For example, in the case of the NaMg$_{0.5}$HPO$_4$ catalyst, 1.0 mole of sodium hydroxide, 0.5 mole of magnesium oxide and 1.0 mole of phosphoric acid were thoroughly mixed with the addition of water. Next, the mixture was evaporated to dryness with stirring, following which the dried mixture was calcined at 500° C. for 6 hours. The resulting solid was comminuted directly or after first molding it into tablets to give the catalyst as granules of 10–16-mesh size. On the other hand, a carrier-supported catalyst was prepared say by comminuting the silica to be used as the carrier into granules of 10–16-mesh size, mixing the comminuted silica with an aqueous solution of the catalyst, evaporating the mixture to dryness, and thereafter calcining the dried granules at 500° C. for 6 hours.

A Pyrex reaction tube having an inside diameter of 12 mm was packed with 2.5–5 cc of the phosphate catalyst thus obtained and secured in an electric furnace held at a prescribed temperature. Next, while passing nitrogen from the top of the reaction tube through the catalyst layer at a gas space velocity of 120 liter/liter/hr, 14% ammonia water was passed through the catalyst layer for 30 minutes at a liquid hourly space velocity of 0.5 liter/liter/hr. The feed of the ammonia water was then stopped, and feed liquids of the same kind as those used in Example 3 were fed from the top of the reaction tube. The gas leaving the catalyst layer was captured by a dry ice trap coupled to the bottom of the reaction tube. The product was quantitatively analyzed by gas chromatography.

In Table 2 are shown the reaction conditions and the results of the reactions. The product yield was shown as molar yield (%) based on the starting α-hydroxycarboxylic acid amide.

TABLE 2

| Run | Catalyst | Feed liquid | LHSV (hr$^{-1}$) | Reaction temperature (°C.) | Product | Yield of product (%) |
|---|---|---|---|---|---|---|
| 33 | Mg$_{0.5}$H$_2$PO$_4$ | A | 0.26 | 370 | methyl methacrylate | 62.0 |
| 34 | CaHPO$_4$ | A | 0.26 | 390 | " | 60.5 |
| 35 | BeHPO$_4$/SiO$_2$ | A | 0.26 | 375 | " | 61.2 |
| 36 | MgHPO$_4$ | B | 0.26 | 300 | methyl methacrylate, methacrylic acid | 10.2 / 68.4 |
| 37 | Mg$_{0.5}$H$_2$PO$_4$/SiO$_2$ | B | 0.26 | 370 | methyl methacrylate methacrylic acid | 17.4 / 64.2 |
| 38 | Ba$_{0.5}$H$_2$PO$_4$ | B | 0.26 | 370 | methyl methacrylate methacrylic | 4.1 / 68.4 |

TABLE 2-continued

| Run | Catalyst | Feed liquid | LHSV (hr$^{-1}$) | Reaction temperature (°C.) | Product | Yield of product (%) |
|---|---|---|---|---|---|---|
| 39 | RbH$_2$PO$_4$/SiO$_2$ | B | 0.26 | 350 | methacrylic acid | 64.8 |
| 40 | Ca$_3$(PO$_4$)$_2$ | C | 0.26 | 360 | " | 51.3 |
| 41 | NaMg$_{0.5}$HPO$_4$ | C | 0.26 | 350 | " | 79.5 |
| 42 | NaH$_2$PO$_4$/SiO$_2$ | C | 0.20 | 325 | " | 78.4 |
| 43 | SrHPO$_4$/SiO$_2$ | C | 0.20 | 325 | " | 82.1 |
| 44 | CsH$_2$PO$_4$/SiO$_2$ | C | 0.20 | 330 | " | 83.5 |
| 45 | MgHPO$_4$/SiO$_2$ | C | 0.26 | 300 | " | 84.8 |
| 46 | K$_3$PO$_4$ | F | 0.26 | 390 | acrylic acid | 45.2 |
| 47 | Ba$_{0.5}$H$_2$PO$_4$/SiO$_2$ | F | 0.20 | 340 | " | 79.5 |
| 48 | Cs$_2$HPO$_4$ | F | 0.26 | 350 | " | 65.6 |
| 49 | KH$_2$PO$_4$/SiO$_2$ | F | 0.26 | 325 | " | 80.1 |
| 50 | Na$_{0.5}$Mg$_{0.25}$—H$_2$PO$_4$ | F | 0.26 | 375 | " | 69.7 |
| 51 | NaMg$_{0.5}$HPO$_4$ | F | 0.26 | 350 | " | 73.5 |
| 52 | LiH$_2$PO$_4$/SiO$_2$ | F | 0.26 | 325 | " | 77.5 |

EXAMPLE 5

Commercial sulfates were calcined at 200°-400° C. for 4 hours. Then, to ensure that they do not absorb moisture they were molded into 10–16-mesh granules in an atmosphere of nitrogen. The catalysts shown in Table 3 were thus obtained.

The mixed sulfate catalysts were obtained in the following manner. An equimolar mixture of two classes of sulfates was thoroughly kneaded together with the addition of water, following which the mixture was dried at 120° C., and thereafter treated in accordance with the procedure described hereinabove to give the catalysts.

A Pyrex reaction tube of 12-mm inside diameter was packed with 2.5–5 cc of the sulfate catalyst and then secured inside an electric furnace held at a prescribed temperature. Next, while feeding nitrogen from the top of the reaction tube at a gas space velocity of 120 liter/liter/hr, the feed liquid was fed at a prescribed liquid hourly space velocity. The feed liquids are the same as those used in Example 3. The gas leaving the catalyst layer were collected by means of a dry ice trap, and the product was quantitatively analyzed by gas chromatography. In Table 3 are shown the reaction conditions and the results obtained. The product yield is shown as molar yield (%) based on the starting α-hydroxycarboxylic acid amide.

TABLE 3

| Run | Catalyst | feed liquid | LHSV (hr$^{-1}$) | Reaction temperature (°C.) | Product | Yield of product (%) |
|---|---|---|---|---|---|---|
| 53 | MgSO$_4$ | A | 0.26 | 375 | methyl methacrylate | 41.2 |
| 54 | CaSO$_4$ | A | 0.26 | 400 | " | 39.8 |
| 55 | Al$_2$(SO$_4$)$_3$ | A | 0.26 | 325 | " | 60.5 |
| 56 | NiSO$_4$ | A | 0.26 | 350 | " | 53.0 |
| 57 | CdSO$_4$.NiSO$_4$ | A | 0.26 | 375 | " | 50.4 |
| 58 | Al$_2$Zn(SO$_4$)$_4$ | B | 0.26 | 375 | " | 40.3 |
| 59 | MgSO$_4$.Na$_2$SO$_4$ | B | 0.26 | 400 | " | 39.0 |
| 60 | Al$_2$(SO$_4$)$_3$/SiO$_2$ | B | 0.26 | 325 | " | 53.2 |
| 61 | Al$_2$(SO$_4$)$_3$.Tl$_2$(SO$_4$)$_3$ | B | 0.26 | 300 | " | 45.4 |
| 62 | Fe$_2$(SO$_4$)$_3$ | C | 0.26 | 350 | methacrylic acid | 60.7 |
| 63 | CuSO$_4$ | C | 0.26 | 375 | " | 35.0 |
| 64 | MgSO$_4$.K$_2$SO$_4$ | C | 0.26 | 375 | " | 36.7 |
| 65 | Al$_2$(SO$_4$)$_3$.In$_2$(SO$_4$)$_3$ | C | 0.52 | 325 | " | 45.1 |
| 66 | Cr$_2$(SO$_4$)$_3$ | F | 0.26 | 350 | acrylic acid | 57.8 |
| 67 | MnSO$_4$.FeSO$_4$ | F | 0.26 | 325 | " | 49.2 |
| 68 | MgSO$_4$.BaSO$_4$ | F | 0.26 | 375 | " | 47.7 |
| 69 | PbSO$_4$.NiSO$_4$ | F | 0.26 | 350 | " | 42.5 |
| 70 | CoSO$_4$ | F | 0.26 | 325 | " | 36.8 |
| 71 | MgSO$_4$.LiSO$_4$ | D | 0.26 | 375 | methyl acrylate | 40.1 |
| 72 | SrSO$_4$.RbSO$_4$ | D | 0.26 | 375 | " | 37.2 |
| 73 | MgSO$_4$.CsSO$_4$ | D | 0.26 | 375 | " | 34.5 |
| 74 | Al$_2$(SO$_4$)$_3$.BeSO$_4$ | D | 0.26 | 350 | " | 48.6 |
| 75 | Fe$_2$(SO$_4$)$_3$ | D | 0.26 | 325 | " | 56.8 |
| 76 | Al$_2$(SO$_4$)$_3$.SnSO$_4$ | D | 0.26 | 350 | " | 47.2 |
| 77 | (NH$_4$)SO$_4$.FeSO$_4$ | D | 0.13 | 300 | " | 37.7 |

EXAMPLE 6

The reactions were carried out as in Example 3 using the oxide catalysts set forth in Table 4. These catalysts were prepared in customary manner. To wit, as starting material of the catalysts, the metal nitrates, metal chlorides, metal oxides and an ammonium salt such as ammonium molbdate were used, and aqueous solutions of the several components were prepared, using these compounds in such amounts as to give the catalyst compositions shown in Table 4. In preparing the aqueous solutions, an aqueous oxalic acid solution was used for dissolving the starting catalysts materials, if necessary. After mixing the aqueous solution of the several components, a carrier was added if necessary, following which the mixtures were evaporated to dryness, dried further at 120° C., and thereafter calcined at 500° C. for 5 hours. All of the catalysts were used as granules of 10–16-mesh size. In the case however of $SiO_2$-26% $Al_2O_3$, $SiO_2$ and $CuO \cdot CuCr_2O_4$ catalysts, the commercially available products were used. In Table 4 the percentage shown in the catalyst composition denotes weight %, and $/SiO_2$ stands for a silica carrier. The compositions of the feed liquids correspond with those used in Example 3. The reaction conditions and the results obtained are shown in Table 4.

The yield of product are shown in mole% based on the starting α-hydroxycarboxylic acid amide.

EXAMPLE 7

Multicomponent oxides were used as the catalyst. Ammonium molybdate, ammonium tungstate, ammonium vanadate, silica-alumina powder (alumina content 26% by weight), cupric nitrate, bismuth nitrate, iron nitrates, cobalt nitrate and 85% phosphoric acid were used as the starting materials for preparing the catalysts. The several starting materials for preparing the catalysts were used in amounts such as to give the catalyst compositions shown in Table 5. After the addition of water, the components were thoroughly mixed while heating the mixture, after which the mixture was evaporated to dryness. The mixture was then molded into pellets and, after drying, calcined at 500° C. for 5 hours.

The pellets were then comminuted into granules of 10–16-mesh size and used as catalysts.

The reactions were then carried out as in Example 6. In Table 5 are shown the reaction conditions and the results obtained.

TABLE 4

| Run | Catalyst | Feed liquid | LHSV (hr$^{-1}$) | Reaction temperature (°C.) | Product | Yield of product (%) |
|---|---|---|---|---|---|---|
| 78 | $SiO_2$—26% $Al_2O_3$ | B | 0.26 | 275 | methyl methacrylate | 49.8 |
| 79 | $Al_2O_3$—15% $B_2O_3$ | B | 0.26 | 300 | " | 51.5 |
| 80 | $SiO_2$—28% MgO | B | 0.26 | 325 | " | 53.7 |
| 81 | $SiO_2 \cdot 12WO_3/SiO_2$ | B | 0.26 | 300 | " | 35.2 |
| 82 | $Al_2O_3$—26% $MoO_3$ | B | 0.26 | 325 | " | 52.1 |
| 83 | $ZrO_2$—10% CdO | C | 0.26 | 350 | methacrylic acid | 23.0 |
| 84 | $Al_2O_3$—10% ZnO | C | 0.26 | 325 | " | 53.1 |
| 85 | $SiO_2$—14% $WO_3$ | C | 0.26 | 325 | " | 54.7 |
| 86 | $Ce_2O_5 \cdot La_2O_3$ | C | 0.26 | 400 | " | 8.5 |
| 87 | $SiO_2$—22% BeO | C | 0.26 | 375 | " | 15.8 |
| 88 | $ThO_2/SiO_2$ | C | 0.26 | 325 | " | 30.5 |
| 89 | $TiO_2$ 15% $Fe_2$—$O_3$ | C | 0.26 | 300 | " | 22.3 |
| 90 | $ZrO_2$ | C | 0.26 | 325 | " | 10.2 |
| 91 | $CuO \cdot CuCr_2O_4$ | C | 0.26 | 350 | " | 20.1 |
| 92 | $TiO_2$—10% NiO | C | 0.26 | 325 | " | 23.5 |
| 93 | $SiO_2$—19% $MoO_3$ | E | 0.26 | 325 | methyl acrylate | 53.2 |
| 94 | $TiO_2$—60% $ZrO_2$ | E | 0.26 | 325 | " | 48.7 |
| 95 | $U_3O_8/SiO_2$ | E | 0.26 | 325 | " | 12.8 |
| 96 | $Al_2O_3$—26% $MoO_3$ | F | 0.26 | 325 | acrylic acid | 55.2 |
| 97 | $TiO_2$—25% $B_{12}O_3$ | F | 0.26 | 350 | " | 25.8 |
| 98 | $Al_2O_3$—25% $Sb_2O_5$ | F | 0.26 | 325 | " | 26.5 |
| 99 | $SiO_2$—14% V O | F | 0.26 | 325 | " | 49.5 |
| 100 | $Y_2O_3/SiO_2$—26% $Al_2O_3$ | F | 0.26 | 325 | " | 38.2 |
| 101 | $Cr_2O_3/Al_2O_3$ | F | 0.26 | 350 | " | 27.3 |
| 102 | $TiO_2$—15% NiO | F | 0.26 | 325 | " | 24.7 |
| 103 | $Al_2O_3$—10% ManO | F | 0.26 | 325 | " | 31.5 |

TABLE 5

| Run | Catalyst | Feed liquid | LHSV (hr$^{-1}$) | Reaction temperature (°C.) | Product | Yield of product (%) |
|---|---|---|---|---|---|---|
| 104 | $Mo_2Cu_1Si_{12}Al_5$ oxide | B | 0.26 | 325 | methyl methacrylate | 45.9 |
| 105 | $Mo_2Cu_1Si_{12}Al_5$ oxide | C | 0.26 | 300 | methacrylic acid | 53.0 |
| 106 | $Mo_1V_1Si_{12}Al_5$ oxide | E | 0.26 | 325 | methyl acrylate | 48.3 |
| 107 | $Mo_1V_1Si_{12}Al_5$ oxide | F | 0.26 | 300 | acrylic acid | 53.6 |
| 108 | $W_2Cu_1Si_{12}Al_5$ oxide | E | 0.26 | 350 | methyl acrylate | 44.5 |
| 109 | $W_2Cu_1Si_{12}Al_5$ oxide | F | 0.26 | 325 | acrylic acid | 49.8 |
| 110 | $Mo_{12}Bi_5Fe_3Co_{10}$—$P_3$ oxide | B | 0.26 | 300 | methyl methacrylate | 45.2 |
| 111 | $Mo_{12}Bi_5Fe_3Co_{10}$— | C | 0.26 | 300 | methacrylic | 51.5 |

TABLE 5-continued

| Run | Catalyst | Feed liquid | LHSV (hr$^{-1}$) | Reaction temperature (°C.) | Product | Yield of product (%) |
|---|---|---|---|---|---|---|
| | P$_3$ oxide | | | | acid | |

EXAMPLE 8

The reactions were carried out as in Example 3, using the catalysts, reaction conditions and alcohols shown in Table 6. The composition of the starting reaction material was α-hydroxyisobutyramide:alcohol:water=1:10:5 (mole ratio).

The reaction conditions and the results obtained are shown in Table 6. The yield of the product is shown as molar yield (%) of the product based on the starting amide.

TABLE 6

| Run | Catalyst | Alcohol | LHSV (hr$^{-1}$) | Reaction temperature (°C.) | Product | Yield of product (%) |
|---|---|---|---|---|---|---|
| 112 | YPO$_4$ | ethyl alcohol | 0.20 | 275 | ethyl methacrylate | 70.1 |
| | | | | | methacrylic acid | 11.4 |
| 113 | " | n-propyl alcohol | 0.20 | 275 | propyl methacrylate | 67.5 |
| | | | | | methacrylic acid | 13.8 |
| 114 | LaPO$_4$ | i-butyl alcohol | 0.20 | 260 | isobutyl methacrylate | 72.6 |
| | | | | | methacrylic acid | 8.2 |
| 115 | " | ethylene glycol | 0.20 | 260 | ethylene glycol monomethacrylate | 67.8 |
| 116 | " | ethylene glycol monomethyl ether | 0.20 | 260 | β-methoxyethyl methacrylate | 69.5 |

EXAMPLE 9

The reactions were carried out in accordance with the reaction procedure of Example 2, using the catalysts, reaction conditions and α-hydroxycarboxylic acid amides shown in Table 7. The composition of the starting material was α-hydroxycarboxylic acid amide:methanol:water=1:10:5 (mole ratio). In Table 7 the reaction conditions and the results obtained are shown. The yield of the product is shown as molar yield (%) of the product based on the starting α-hydroxycarboxylic acid amide.

TABLE 7

| Run | Catalyst | α-Hydroxycarboxylic acid amide | LHSV (hr$^-$) | Reaction temperature (°C.) | Product | Yield of product (%) |
|---|---|---|---|---|---|---|
| 117 | LaPO$_4$ | α-hydroxybutyramide | 0.20 | 290 | methyl β-methacrylate | 81.2 |
| 118 | YPO$_4$ | α-hydroxyisovaleramide | 0.20 | 275 | methyl β, β-dimethacrylate | 79.5 |
| 119 | MgHPO$_4$ | α-methyl-α-hydroxybutyramide | 0.20 | 300 | β-methyl methaacrylic acid | 65.8 |

EXAMPLE 10

Zirconium oxychloride (ZrOCl$_2$.8H$_2$O) (36.1 g, 0.112 mole) was dissolved in 50 ml of water. Separately, monosodium phosphate (NaH$_2$PO$_4$.2H$_2$O) (156 g, 1 mole) was dissolved in 200 ml of 3 N hydrochloric acid followed by heating the resulting solution to 80° C. The former solution was then added to the latter solution with stirring to form a white precipitate. After continuing the stirring for a further one hour, the white precipitate was thoroughly water-washed by the decantation method, after which it was filtrably separated and washed in water. After drying the white precipitate at 120° C., it was calcined in air at 400° C., and thereafter molded into granules of 10–16-mesh size to prepare a Zr(HPO$_4$)$_2$ catalyst. Next, lanthanum oxide (La$_2$O$_3$) (0.065 mole) was completely dissolved in an aqueous nitric acid solution, after which the resulting solution was concentrated by heating to prepare lanthanum nitrate, to which 400 cc of water was added to form an aqueous lanthanum nitrate solution. When 100 cc of an aqueous solution containing 20.3 g (0.143 mole) of sodium hydrogenphosphate (Na$_2$HPO$_4$) was added to the aqueous lanthanum nitrate solution, a white precipitate formed. The precipitate thus obtained was stirred at 80° C. for one hour, after which it was thoroughly washed in water. The precipitate was separated by filtration, water-washed and dried at 120° C. The white precipitate was then calcined in a stream of air at 400° C. for 6 hours. The calcined product was then molded into granules of 10–16-mesh size to prepare a LaPO$_4$ catalyst.

A Pyrex reaction tube (9) having an inside diameter of 12 mm, as shown in the drawing, was used. The Zr(HPO$_4$)$_2$ catalyst (5 cc) was packed in the tube as a second-stage reaction layer (6), and 5 cc of the LaPO$_4$ catalyst was packed as a first-stage catalyst layer (5). The evaporation part (4) of the reaction tube was packed with molten alumina balls 3 mm in diameter. The reaction tube was then secured in an electric furnace capable of adjusting the temperatures of the first-stage and second-stage catalyst layers independently of each other and was coupled, as shown in FIG. 1, with a reaction mixture receptacle (7) immersed in a dry ice trap (8). Nitrogen was then passed at a rate of 40 ml per was thoroughly water-washed, filtered, dried, calcined at 500° C. for 5 hours, and comminuted into 10–16-mesh particles.

TABLE 8

| Run | 1st-stage catalyst layer Class of catalyst | Reaction temperature (°C.) | 2nd-stage catalyst layer Class of catalyst | Reaction temperature (°C.) | Yield of reaction product (mole %) Methyl methacrylate | Acetone | Dimethyl ether* |
|---|---|---|---|---|---|---|---|
| 120 | YPO$_4$ | 275 | Zr(HPO$_4$)$_2$ | 275 | 88.4 | 9.5 | 0.0 |
| 121 | CePO$_4$ | 275 | Zr(HPO$_4$)$_2$ | 275 | 89.2 | 8.4 | 0.0 |
| 122 | AlPO$_4$ | 320 | Zr(HPO$_4$)$_2$ | 275 | 85.1 | 12.1 | 0.0 |
| 123 | PrPO$_4$ | 275 | TiPO$_4$ | 275 | 89.0 | 8.5 | 0.2 |
| 124 | Mg(H$_2$PO$_4$)$_2$ | 275 | TiO$_2$ | 330 | 82.8 | 9.5 | 0.0 |
| 125 | SiO$_2$—MgO | 270 | ZrO$_2$ | 300 | 80.6 | 10.2 | 0.0 |

*Although dimethyl ether is not a product derived from α-hydroxyisobutyramide, for convenience' sake the amount formed of dimethyl ether has been shown in mole % based on α-hydroxyisobutyramide.

minute through the catalyst layers via a carrier gas feed tube (3) located at the upper part of the reaction tube, while the temperatures of both the first and second stages were raised to 275° C. Methanol was then fed into the reaction tube at a rate of 1.5 g per hour via a material feed tube B (2) shown in the drawing, followed by feeding an aqueous α-hydroxyisobutyramide solution of 45 wt. % concentration at a rate of 1.0 g per hour via a material feed tube A (1). Three to four hours after the initiation of the feeding of the starting materials, a reaction mixture was collected at the dry ice trap (8) and analyzed by gas chromatography. It was found that the molar yield of methyl methacrylate was 89.0% based on the starting α-hydroxyisobutyramide. As by-products other than methyl methacrylate, only 8.4%, based on the α-hydroxyisobutyramide, of acetone was found. No dimethyl ether was detected.

EXAMPLE 11

The experiments were conducted using the same apparatus and procedure as described in Example 10, except that the catalysts and reaction temperatures were varied as shown in Table 8. The results obtained are shown in Table 8. The phosphate catalysts used were prepared in customary manner. To wit, a metal nitrate, metal chloride or metal oxide and 85% phosphoric acid or a phosphate were directly reacted in an aqueous solution, following which the reaction mixture was evaporated to dryness, or a phosphate was separated from the aqueous solution and water-washed, to obtain a solid, which was thoroughly dried at 120° C. The phosphates thus obtained and commercially available phosphates were molded into pellets and calcined at 250°–600° C. for 5 hours. The catalysts were then prepared by comminuting the calcined product into 10–16-mesh granules. On the other hand, the SiO$_2$-MgO catalyst was prepared in the following manner. An aqueous magnesium chloride solution was added to an aqueous sodium silicate solution to form a precipitate, after which the precipitate was thoroughly water-washed, filtered, dried, calcined at 500° C. for 5 hours, and comminuted into 10–16-mesh particles. The TiO$_2$ catalyst was prepared by adding and dissolving TiCl$_4$ in cold water followed by hydrolyzing the solution by heating to yield a precipitate, which was then thoroughly water-washed, filtered, dried, calcined at 500° C. for 5 hours, and comminuted into 10–16-mesh particles. The ZrO$_2$ catalyst was prepared in the following manner. Ammonia water was added to an aqueous ZrOCl$_2$ solution, after which the resulting precipitate

COMPARATIVE EXAMPLE 1

The relationship between the amount of methyl methacrylate formed and the amount of dimethyl ether formed as a by-product when α-hydroxyisobutyramide, water and methanol were fed together to a single catalyst layer was examined. Using the same apparatus as that used in Example 10, the first-stage catalyst layer was packed with molten alumina balls of 3-mm diameter, while the second-stage catalyst layer was packed with 5 cc of the same catalysts as those used in the foregoing example. An aqueous α-hydroxyisobutyramide solution and methanol were then fed together at rates of 1.0 g per hour and 1.5 g per hour, respectively, from the material feed tube A shown in the drawing. The experiment was otherwise carried out as in Example 10. The results obtained are shown in Table 9.

TABLE 9

| Run | Class of catalyst | Reaction temperature (°C.) | Yield of reaction product (mole %) Methyl methacrylate | Dimethyl ether |
|---|---|---|---|---|
| 126 | YPO$_4$ | 275 | 82.3 | 70 |
| 127 | LaPO$_4$ | 275 | 84.5 | 35 |
| 128 | AlPO$_4$ | 375 | 80.3 | 25 |
| 129 | Mg(H$_2$PO$_4$)$_2$ | 370 | 64.9 | 85 |
| 130 | Zr(HPO$_4$)$_2$ | 300 | 58.0 | 5 |
| 131 | TiPO$_4$ | 300 | 36.0 | 2 |
| 132 | ZrO$_2$ | 350 | 10.2 | 1 |
| 133 | TiO$_2$ | 330 | 8.3 | 1 |

What is claimed is:

1. A process for producing an α,β-unsaturated carboxylic acid which consists essentially of contacting an α-hydroxycarboxylic acid amide having the formula:

wherein R$_1$ and R$_2$ each is a member selected from the group consisting of hydrogen and an alkyl group, with the proviso that at least one of R$_1$ and R$_2$ is an alkyl group, with a solid acid catalyst consisting essentially of at least one phosphate of an element selected from group III(b), the lanthanide group and the actinide group of the periodic table, said contact being carried out independently or along with water vapor at a temperature between 150° and 500° C.

2. The process as claimed in claim 1 wherein said α-hydroxycarboxylic acid amide is a member selected from the group consisting of lactimide, α-hydroxybutyramide, α-hydroxyisobutyramide, α-hydroxyvaleramide, α-hydroxyisovaleramide, α-methyl-α-hydroxybutyramide and α,γ-dimethyl-α-hydroxybutyramide.

3. The process as claimed in claim 1 wherein 1 to 50 moles of said water vapor is used per mole of said α-hydroxycarboxylic acid amide.

4. The process as claimed in claim 1 wherein the contacting is conducted at a temperature between 200° and 450° C.

5. A process for producing an α,β-unsaturated carboxylic acid ester which consists essentially of contacting an α-hydroxycarboxylic acid amide having the formula:

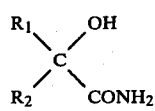  (I)

wherein $R_1$ and $R_2$ each is a member selected from the group consisting of hydrogen and an alkyl group, with the proviso that at least one of $R_1$ and $R_2$ is an alkyl group, with a solid acid catalyst consisting essentially of at least one phosphate of an element selected from group III(b), the lanthanide group and the actinide group of the periodic table, said contact being arried out along with an aliphatic alcohol or along with an aliphatic alcohol and water vapor at a temperature between 150° and 500° C.

6. The process as claimed in claim 5 wherein said α-hydroxycarboxylic acid amide is a member selected from the group consisting of lactamide, α-hydroxybutramide, α-hydroxyisobutyramide, α-hydroxyvaleramide, α-hydroxyisovaleramide, α-methyl-α-hydroxybutyramide, and α,α-dimethyl-α-hydroxybutyramide.

7. The process as claimed in claim 5 wherein said aliphatic alcohol is a member selected from the group consisting of methyl alcohol, ethyl alcohol, n-propyl alcohol, i-propyl alcohol, n-butyl alcohol and t-butyl alcohol.

8. The process as claimed in claim 5 wherein 1 to 50 moles of said water vapor is used per mole of said α-hydroxycarboxylic acid amide and 1 to 50 moles of said aliphatic alcohol is used per mole of said α-hydroxycarboxylic acid amide.

9. The process as claimed in claim 5 wherein the contacting is conducted at a temperature between 200° and 450° C.

10. A process for producing an α,β-saturated carboxylic acid ester which consists essentially of catalytically reacting an α-hydroxycarboxylic acid amide having the formula:

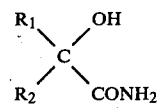  (I)

wherein $R_1$ and $R_2$ each is a member selected from the group consisting of hydrogen and an alkyl group, with the proviso that at least one of $R_1$ and $R_2$ is an alkyl group, with a first solid acid catalyst consisting essentially of at least one phosphate of an element selected from group III(b), the lanthanide group and the actinide group of the periodic table, alone or along with water vapor at a temperature of between 150° and 500° C., and then catalytically reacting the resulting reaction mixture with a second solid acid catalyst consisting of at least one member selected from the group consisting of at least one phosphate of a metallic element of group III(a), group IV(b) and group VI(b) of the periodic table, an oxide of an element of group IV(b), and a compound oxide of silicon oxide and an oxide of an element of group III(a) or group IV(b), along with an aliphatic alcohol at a temperature between 150° and 500° C.

11. The process as claimed in claim 10 wherein said α-hydroxycarboxylic acid amide is a member selected from the group consisting of lactimide, α-hydroxybutyramide, α-hydroxyisobutyramide, α-hydroxyvaleramide, α-hydroxyisovaleramide, α-methyl-α-hydroxybutyreamide and α,γ-dimethyl-α-hydroxybutyramide.

12. The process as claimed in claim 10 wherein said aliphatic alcohol is a member selected from the group consisting of methyl alcohol, ethyl alcohol, n-propyl alcohol, i-propyl alcohol, n-butyl alcohol and t-butyl alcohol.

13. The process as claimed in claim 10 wherein 1 to 50 moles of said water vapor is used per mole of said α-hydroxycarboxylic acid amide and 1 to 50 moles of said aliphatic alcohol is used per mole of said α-hydroxycarboxylic acid amide.

14. The process as claimed in claim 10 wherein the contacting is conducted at a temperature between 200° and 450° C.

15. Composition comprising an α-hydroxycarboxylic acid amide having the formula:

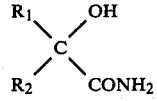  (I)

wherein $R_1$ and $R_2$ each is a member selected from the group consisting of hydrogen and an alkyl group, with the proviso that at least one of $R_1$ and $R_2$ is an alkyl group, with a first solid acid catalyst consisting essentially of at least one phosphate of an element selected from group III(b), the lanthanide group and the actinide group of the periodic table.

16. Composition as claimed in claim 15 wherein an aliphatic alcohol is also present.

* * * * *